United States Patent [19]

Häuselmann et al.

[11] Patent Number: 5,658,343
[45] Date of Patent: Aug. 19, 1997

[54] AREAL IMPLANT

[75] Inventors: Hans Jörg Häuselmann, Bremgarten, Switzerland; Mats Paulsson, Cologne, Germany; Peter Bittmann; Thomas Thaler, both of Zürich, Switzerland

[73] Assignee: Sulzer Medizinaltechnik AG, Winterthur, Switzerland

[21] Appl. No.: 472,699

[22] Filed: Jun. 6, 1995

[30] Foreign Application Priority Data

Jul. 11, 1994 [EP] European Pat. Off. .............. 94810408

[51] Int. Cl.$^6$ ............................................. A61F 2/38
[52] U.S. Cl. ................................ 623/20; 623/11
[58] Field of Search ........................ 623/11, 20, 39, 623/42, 46, 36, 17; 5/420, 457, 458

[56] References Cited

U.S. PATENT DOCUMENTS 3,867,728  2/1975  Stubstab et al. .............. 623/17

FOREIGN PATENT DOCUMENTS

WO90/12603  11/1990  WIPO.
WO94/09722  5/1994  WIPO.

*Primary Examiner*—Robert A. Clarke
*Attorney, Agent, or Firm*—Townsend and Townsend and Crew LLP

[57] ABSTRACT

This invention provides an implant (prosthesis) for the replacement of defective biological tissue part. In particular, the implants of this invention are well suited for the replacement of cartilage, more preferably for the replacement of articular cartilage. In one embodiment, the implants comprise a micromatrix constructed from an upper boundary layer and a lower boundary layer where the upper and said lower boundary layers are connected via an intermediate layer with fibers. The implant also includes a nanomatrix situated within the intermediate layer. The nanomatrix contains elements of a size on the order of magnitude of nanometers. The intermediate layer accommodates the nanomatrix such that, for a growing inner pressure the boundary layers are mutually held at a preset distance from one another.

57 Claims, 7 Drawing Sheets

AREAL IMPLANT

FIELD OF THE INVENTION

This invention relates to a plane or areal implant (prosthesis) for the replacement of defective biological tissue parts. In particular, this invention provides implants for the replacement of articular cartilage.

BACKGROUND OF THE INVENTION

Methods and artificial matrices for the growth and implantation of cartilaginous structures and surfaces of bone are described in PCT patent application WO 90/12603. This application describes artificial matrices in which cell cultures are prepared in vitro. The cell cultures develop into a cartilage-like mass after subsequent transplantation into a mammal.

The disclosed implants are useful for the replacement of cartilage parts at the ear and nose where the cartilage has a pure space holding function with a low mechanical load. However, articular cartilages or joints are subjected to larger mechanical loads which go beyond a space holding function.

SUMMARY OF THE INVENTION

This invention provides an implant (prosthesis) for the replacement of defective biological tissue part. In particular, the implants of this invention are well suited for the replacement of cartilage, more preferably for the replacement of articular cartilage. In one embodiment, the implants comprise a micromatrix constructed from an upper boundary layer and a lower boundary layer where the upper and lower boundary layers are connected via an intermediate layer with fibers. The implant also includes a nanomatrix situated within the intermediate layer. The nanomatrix contains elements of a size on the order of magnitude of nanometers. The intermediate layer accommodates the nanomatrix such that, for a growing inner pressure the boundary layers are mutually held at a preset distance from one another.

The nanomatrix can contain cells that produce an extracellular matrix production of which tends to increase the volume of the implant. The nanomatrix can also absorb water e.g., because of the presence of charged molecules. Because the boundary layers are held at a preset distance the absorption of water and/or the production of extracellular matrix increases the internal pressure of the implant rather than producing a change in volume. The implant is thereby prestressed (e.g., up to a pressure of several bars which is in excess of the physiological pressures usually prevailing in tissues) and tends to resist compressive loads as occur in a joint. When the prestressed implant is loaded it may accommodate the load by partially deforming with the loss of water through the boundary layer(s). Further deformation is resisted however through the tendency of the implant to absorb water. The implant achieves an equilibrium between physical pressure and a binding mechanism for the water molecules which provides a source of pressure in the partially saturated nanomatrix. Thus, the implants of this invention act in a manner analogous to that of naturally occurring cartilage.

The implants of this invention can also contain cells (e.g., chondrocytes) that produce an extracellular matrix. In addition, the implants can contain collagen fibers. The formation of collagen fibers and proteoglycan is promoted through the increased inner pressure of the implant which results in the formation of a cartilage-like structure in the nanomatrix. As will be explained herein, these advantages and others are provided by the present invention.

BRIEF DESCRIPTION OF THE DRAWINGS

FIG. 5a illustrates a hook-like needle 16 piercing a non woven fabric 23 whereby a loop of thread 24 around the needle 16 is held back by the fabric 23. FIG. 5b shows the hook-like head of the needle 16 on the opposite side of the fabric 23 and a guide bar leading the thread 17 across the hook, whereby more thread 24 can be delivered when tension is applied. FIG. 5c shows the needle 16 on its back travel where the hook-like needle head is closed to permit the thread 24 to be pulled through the fabric 23. FIG. 5d shows the, closed needle pulled back through the fabric 23 forming another loop of thread 24 which passes through the former loop (knocking over). FIG. 5e shows the needle 16 waiting for the non woven fabric 23 to move perpendicularly to the needle by one step. After that step the needle will open the hook-like head so that the loop of thread lays freely around its body. A new stitching cycle can then start.

FIG. 9a shows that a fabric that already has a coherent structure can be provided with an additional upper boundary layer of polyurethane. The fabric is laid into a flat shell 37 and covered to its top 38 with dissolved polyurethane 36, which under special conditions concentrates as a membrane at the liquid level and encloses the fibers at the top. FIG. 9b illustrates a shell 37 with a fabric 35 at its bottom 39. Dissolved polyurethane particles 43 move into the upper boundary layer forming a membrane 15, which encloses the fibers at the top and makes connections at points of contact 8 of fibers. With a wet atmosphere 41 on top of the shell 37, pores 42 can be generated which can be preserved by lyophilization.

DETAILED DESCRIPTION

Figure 1:
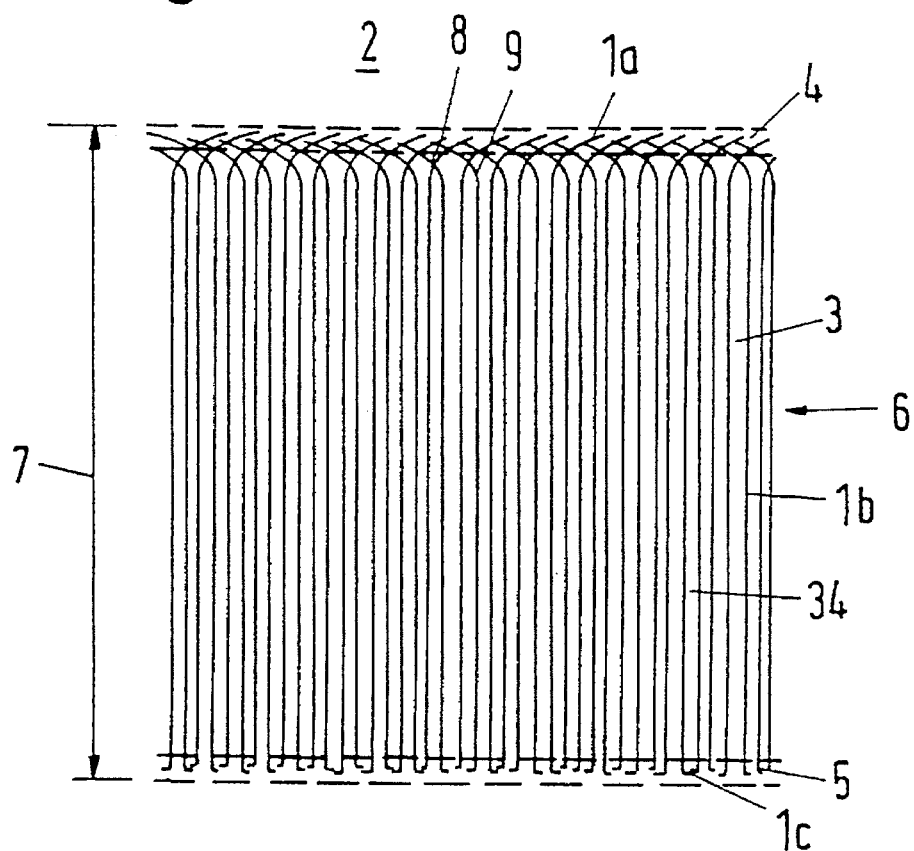
FIG. 1 shows a schematic illustration of the design of a micromatrix with an intermediate layer as well as a lower and an upper boundary layer.

It is an object of the present invention to provide an implant which to a large degree takes on the compressive characteristics and the tensile elastic characteristics of natural articular cartilage. The mechanical properties of natural articular cartilage are well known to those of skill in the art and are, for example, described in "Knee Meniscus, Basic and Clinical Foundations", Raven Press Ltd. 1992, Chapters 2 and 4, and in "Articular Cartilage and Knee Joint Function, Basic Science and Arthroscopy", Raven Press Ltd., 1990, Chapters 1 and 2.

The implants of this invention are characterized by a micromatrix which is initially constructed from an upper and a lower boundary layer. An intermediate layer containing fibers having a diameter on the order of micrometers is provided between the boundary layers. The intermediate layer keeps the boundary layers at a provided distance from one another when the pressure builds up within the micromatrix. The pressure build-up therein arises from a nanomatrix containing elements which are of a size on the order of nanometers. The elements can be present as interlaced structures in the intermediate layer and are retained via the boundary layers as well as via a barrier or membrane which is pervious to liquids. Suitable elements of a nanomatrix are described in the Journal of Cell-Science 107, pages 17 to 27 (1994) with the report entitled "Phenotypic stability of bovine articular chondrocytes after long-term culture in alginate beads".

The implants (prostheses) of this invention are advantageous in that, depending on the behavior of the nanomatrix, they provide a cartilage-like cushion which is stable in shape and yet prestressed. The characteristics of-this cushion are similar to a natural cartilage in which a partial collapse (compression) is possible through the liberation of water molecules during an increased pressure load from the outside. The water thus liberated is replaced causing a new increase in volume and pressure occur during periods in which the implant is weakly loaded.

The implants of this invention build up an internal pressure of up to several bars, which is higher than the physiological pressures usually prevailing in the tissue. This excess pressure builds up in the intermediate layer (e.g., through uptake and binding of water) and corresponds to a state of equilibrium between physical pressure on the implant and a binding mechanism for water molecules, i.e. a source pressure of the partially saturated nanomatrix molecules.

The formation of collagen fibers and proteoglycan is promoted through the increased inner pressure and facilitates the formation of a cartilage-like structure in the implant. This is of advantage particularly in the region of the boundary layers where the newly formed collagen structures can to a large degree take over the mechanical functions of the micromatrix in the boundary layer and bordering intermediate layer. Particularly, when the micromatrix in the boundary layer comprises a biologically decomposable material, the newly formed collagen structures take over the mechanical function of the boundary layer and bordering intermediate layer of the micromatrix as the decomposable material is lost.

Biologically decomposable materials are well known to those of skill in the art. For example, the following materials as well as their copolymers and their mixed polymers are suitable as biologically decomposable materials in this invention: polylactic acid, polyglycolic acid, $\epsilon$-caprolactone and polydioxanone.

The boundary layers of the implant have a greater fiber density than the fiber density in the intermediate layer. The boundary layers are structured such that they resist a tensile load in the surface such as that existing during elevated inner and/or outer pressure.

The volume increase in the nanomatrix which leads to the increase in internal pressure can be brought about by a variety of different mechanisms. For example, macromolecules with negative charges can be dispersed in the nanomatrix, so that because of the Donnan-effect, water molecules from the surrounding liquid travel into the nanomatrix.

The volume increase can also be caused through the creation of newly synthesized extracellular matrix produced by cells which are dispersed in vitro in the nanomatrix or simply through the growth and/or proliferation of such cells. In both methods, a gel can be incorporated in the structure of the nanomatrix which on the one hand takes over a partial function of the extracellular matrix and on the other hand acts as a diluent during the sowing of the cells in order to attain a desired uniform concentration during the construction of the micromatrix. The gel can also be composed so as to maintain (guarantee) the phenotypical stability of the cells which thus, in a preferred embodiment, remain chondrocytes.

Alginate provides a suitable initial matrix in the implants of this invention. The alginate will contain and support the dispersed cells which then form natural matrix molecules corresponding to the matrix produced in vivo.

The increased fiber density in the boundary layer, can be caused by bending or folding the micro fibers of the intermediate layer so that they lie in the boundary layer where they are interlaced. Cuts in the boundary layer and in planes parallel to the boundary layer, will produce a surface part which is covered by fibers.

A fiber having a merely circular cross-section proportional to the square of its radius in the intermediate layer can have a cross-section parallel to the plane of the boundary layer which is proportional to its diameter and to the length of the fiber positioned in the boundary layer. In this case it is advantageous if the microfibers of the intermediate layer form an arch in the boundary layer, because then the fibers which are embedded into the nanomatrix are not only just compressed during a pressure load from the outside, but are also loaded by bending and tension when the boundary layer yields towards the interior of the implant.

The boundary layer can also comprise a membrane which is pervious to liquids, which is connected with the micro fibers of the intermediate layer. In this instance, for example, the micro fibers can be formed as a non-woven fabric or fleece which is thermally melted to the membrane or welded with the same.

In another embodiment, a boundary layer is comprises a woven or a knitted fabric which is welded with the microfibers of the intermediate layer. The weld zones can be created by drawing the combined intermediate layer and the boundary layer over a needle drum with heated needles. The submerging needle tips create weld points. The two layers can also be connected by partial dissolution with a solvent, by bonding with a body-compatible adhesive, such as a fibrin adhesive (Tissucol®), or textile glutaminase (a cross-linking enzyme), or by sewing with a biocompatible thread. If the connection (particularly a sewed connection) is effected over a large area e.g., over both boundary layers with microthreads, then the intermediate layer can also accommodate a non-woven fabric as a space holder.

Embodiments of a micromatrix which can be manufactured in one work cycle are particularly advantageous. In one such embodiment, a micromatrix with two more dense boundary layers woven in two planes on a narrow-fabric loom for velvet bands is manufacturable, if the cutting operation which is customary in the case of velvet is omitted. The microfibers of the intermediate layer are formed from the pile threads, while the boundary layers of the micromatrix come about in the upper and lower weaving plane. In this manner, the warp yarns in one plane can differ in their titre, in the number of filaments, and in the material. In this respect, certain warp yarns can also be metallic, for example made from titanium, in order to promote ingrowth of bone material.

Another method of manufacture of the micromatrix consists of knitting in two planes as for example on a double-bar raschel knitting machine.

The fibers of the micromatrix must be biocompatible and can for example be formed polyethylene-terephtalate, polyetherketone, polypropylene, teflon, carbon, or polyethylene. If the same materials are processed in the boundary layers as threads with a plurality of fibrils, such as during weaving in two planes, fairly fine screen structures are brought about in order to accommodate the nanomatrix. The nanomatrix can then include macromolecules such as proteoglycan-aggregates with molecular weights of 50 to 100 million Daltons. The macromolecules control the volume and water absorption in the nanomatrix. The nanomatrix can also be provided with cell structures such as chondrocytes in order to bring about volume changes and pressure changes through the newly formed nanomatrix.

The invention is now described in detail with reference to the drawings. The drawings illustrate different embodiments of a tensile resistant pressure maintaining micromatrix 2 its manufacture, and mechanisms for the increase in volume of a pressure stable nanomatrix 3. The nanomatrix 3 is embedded in a shape-maintaining micromatrix 2 between an upper boundary layer 4 and a lower boundary layer 5. The nanomatrix can bring about an increase in volume and respectively and increase of pressure within the micromatrix 2 through the absorption or addition of water molecules to the newly formed nanomatrix. Through the use of a textile micromatrix with an intermediate layer 6, a planar formation which is under an inner pressure arises. The planar formation (areal implant) develops pressure resilient characteristics similar to the cartilage layer of a joint and thus provides an effective a replacement for defective cartilage parts.

In FIG. 1, a micromatrix 2 is shown with an upper boundary layer 4 in which fibers 1a lie and a lower boundary layer 5 in which fibers 1c lie. The micromatrix also comprises an intermediate layer 6 which is formed by bent fibers 1b. Upper and lower boundary layers 4 and 5 are held at a constant distance 7 of for example 2 mm by the fibers 1b of the intermediate layer 6. A newly formed nanomatrix is imbedded in the intermediate layer 6 and extends up into the boundary layers 4 and 5. The newly formed nanomatrix causes an increase in volume through the absorption or addition of water molecules, which leads to an increase in the internal pressure 34 of the intermediate layer 6. The fibers 1b change into fibers 1a of the upper boundary layer 4 in an arc 9 and thus contribute to the increased fiber density of the upper boundary layer. The fibers in the boundary layer, in combination with the fibers in the nanomatrix, provide a body that has sufficient strength to resist the normal (unloaded) internal pressure 34 of the prestressed implant and also the pressures resulting from an externally imposed shock-like load.

Such a micromatrix can be manufactured in a variety of different ways. If microfibers 1a, 1b, 1c contribute to the formation, then they advantageously have a plurality of fibrils and a twisting of few revolutions per meter, in order to obtain a more likely flat lens-shaped cross-section at the redirections in the boundary layer.

Figure 2:
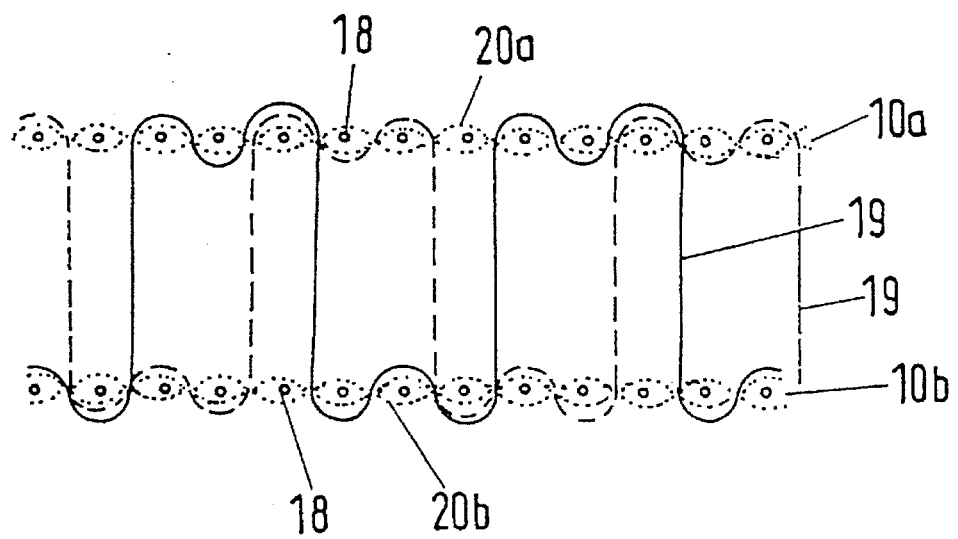
FIG. 2 schematically illustrates the weave during the manufacture of a micromatrix on a narrow-fabric loom for velvet, in which the cutting operation is omitted.

A narrow-fabric loom for velvet brings about the desired fine structures. FIG. 2 shows ribbon looms in an upper plane 10a and a lower plane 10b, which each respectively correspond to the boundary layers 4 and 5 containing fibers 1a and 1c, wherein warp yarns 20a, 20b extend in these planes and are bound by weft yarns 18. Pile threads 19 connecting the upper and lower plane 10a, 10b form the fibers 1b in the intermediate layer. Bar looms for velvet which can produce such a fabric are for example manufactured by the firm Jacob Müller AG, CH-5262 Frick (Switzerland). Through elimination of the cutting operation which is necessary for velvet, a double-walled fabric arises which is held together through the pile threads. In the course of this, warp yarns 20 having a plurality of fibrils and comprising different materials are also possible. For example, metallic warp yarns 20b can thus also be processed in the lower plane 10b, which, if they are formed from titanium, provide an advantageous surface for the ingrowth of bones.

Figure 3:
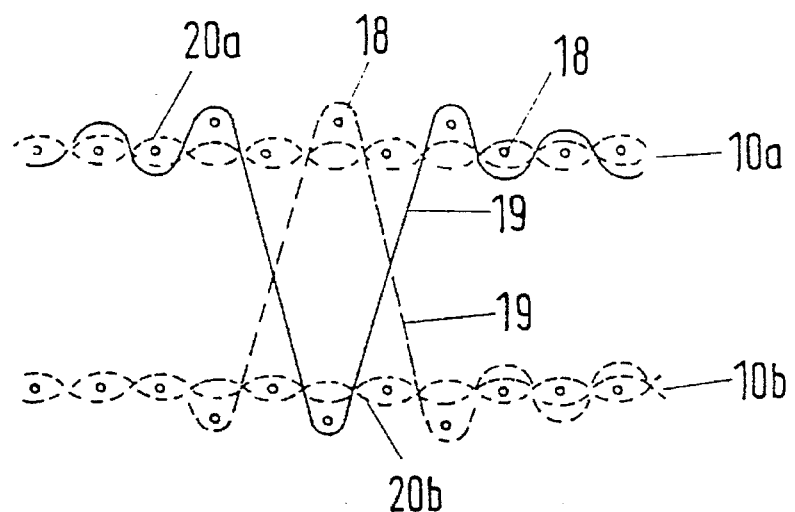
FIG. 3 schematically, a type of connection formed during the manufacture of a duplex-wall fabric with a warp yarn system and with double grippers.

The situation for a micromatrix in accordance with the FIG. 3 is similar. The micromatrix is manufactured on a miniaturized embodiment of a weaving machine with a warp yarn system and double grippers for duplex-wall fabrics, wherein only narrow widths, up to 50 mm such as for the narrow-fabric loom, are necessary in order to obtain replacement parts for natural cartilage. This can also be done with upper warp yarns 20a in an upper plane 10a and with lower warp yarns 20b in a lower plane 10b, where additional pile threads 19 are tied up in the warp yarns 20a, 20b via picks 18.

Figure 4:
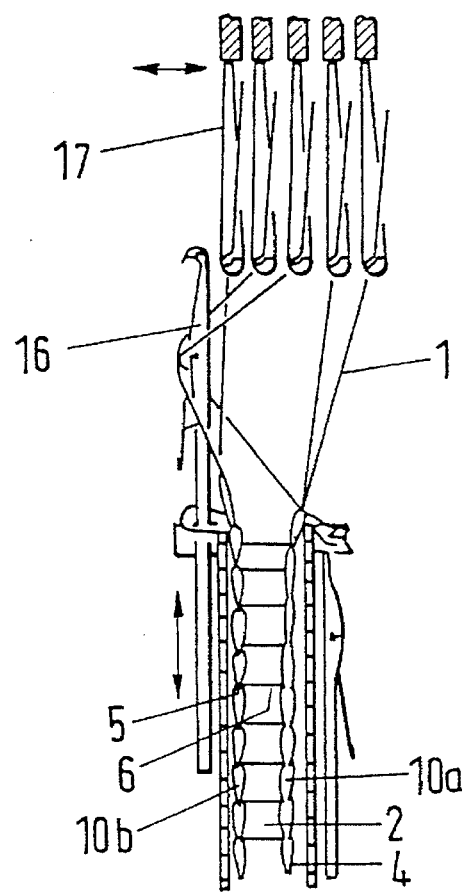
FIG. 4 illustrates the arrangement of latch needles and guide bars during the manufacture of loop cut plush on a double-bar raschel hitting machine.
Figure 5A:
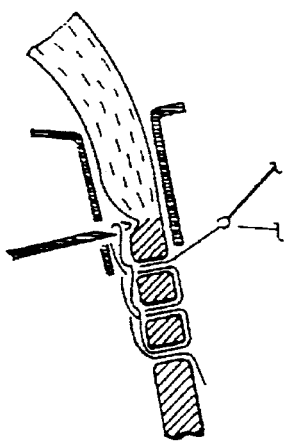
FIGS. 5a, 5b, 5c, 5d, and 5e illustrate a stitch-bonding cycle used in the manufacture of a micromatrix from a fleece by stitch bonding.
Figure 5B:
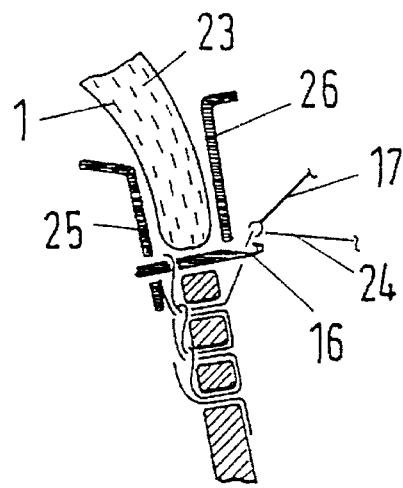
Figure 5C:
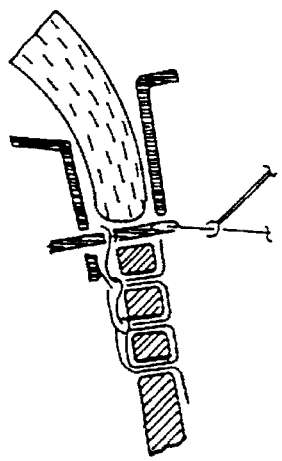
Figure 5D:
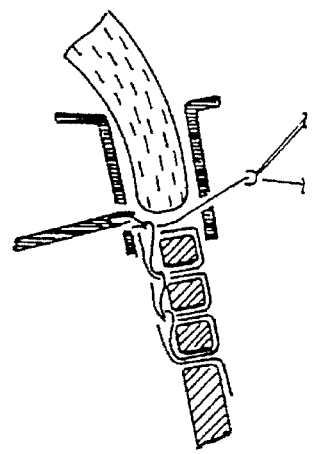
Figure 5E:
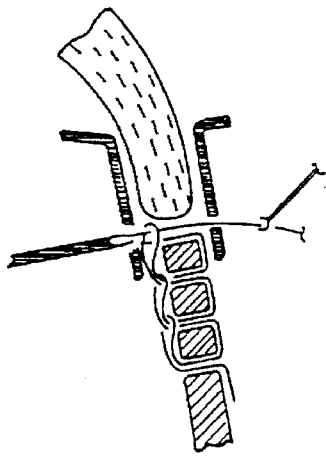

FIG. 4, shows the manufacture of a knitted micromatrix 2 on a double-bar raschel knitting machine which is otherwise typically used for the manufacture of loop cut plush. The fibers 1 are processed in an upper and lower plane, 10a and 10b, to form an upper and lower boundary layer, 4 and 5, and into an intermediate layer 6 via latch needles 16 and guide bars 17, respectively.

In another embodiment, micromatrix 2 starts out from a non-woven fabric which is processed into a mat through stitch-bonding. The principle stitch-bonding cycle is described in FIG. 5. A non-woven fabric 23 is guided over funnel-shaped boundaries 25, 26 and sewn to a mat with threads 24 through needles 16 and guide bars 17. The work cycles are a) piercing, b) folding, c) closing of the needle heads, d) knocking-over, e) take-down of the mat. The relatively wide loops of the sewing threads are meant as a support from the non-woven fabric in the transverse direction, where further supports between points of contact 8 of the fibers 1 in the non-woven fabric are provided. These are manufactured by partial dissolution with a solvent or by bonding with an adhesive. These loops which rise up to and into the intermediate layer.

Figure 9A:
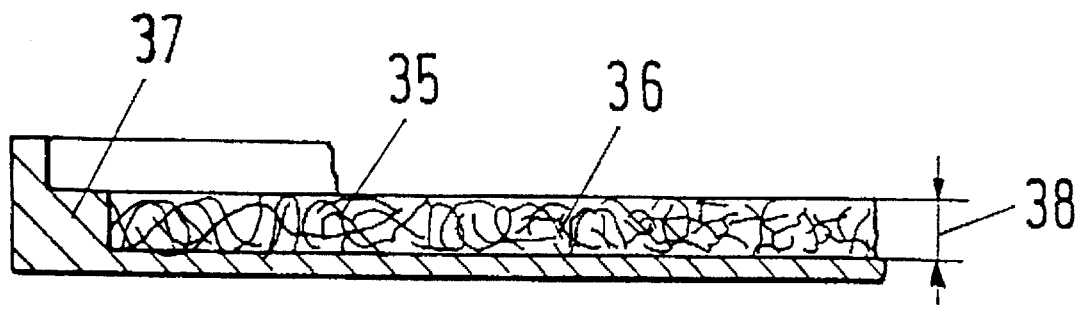
FIGS. 9a and 9b schematically illustrate the manufacture of a membrane of a non-woven fabric.
Figure 9B:
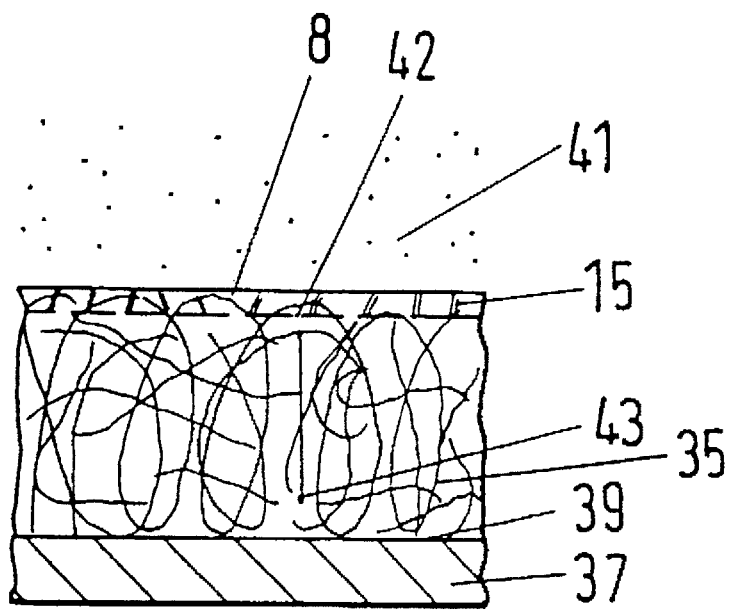

A special upper boundary layer in the form of a membrane 15 with pores 42 in the size of 5 to 10 μm is manufactured with polyurethane in accordance with the FIGS. 9a and 9b. A non-woven fabric 35, a knitted fabric or a woven fabric with a depth 38 of for example 3 mm is spread in a shell 37, and this is filled up to the topmost fibers with dimethylformamide containing 5% to 10% polyurethane dissolved therein dissolved. A damp atmosphere is maintained above the solution. The damp atmosphere causes the strongly hygroscopic dimethylformamide in the boundary layer to hydrate and at the same time lowers the solubility of polyurethane. This makes a sponge-like area from the polyurethane in the form of a membrane with a microstructure. The polyurethane particles 43 which are deeper (closer to the bottom 39 of the shell 37) are mobile at temperatures of ca. 50° C. such that they migrate into the upper boundary layer. Thus, a boundary layer of up to 0.3 mm thickness is formed which has pores 42 and which ties up the fibers of the intermediate layer. The pore structure in the upper boundary layer can be preserved through lyophilization.

Such a membrane 15 supports the nanomatrix during the formation of an internal pressure. Where this membrane is manufactured from biocompatible and resorbable material and used with a nanomatrix comprising a proteoglycan-aggregate and collagen fibrils, the membrane initially provides support, yet regresses with the growing load capacity of the collagen structure which forms in the upper boundary layer, i.e. it is slowly dissolved by the organism when it is implanted in vivo.

Hydrogels which occur linearly or in a branched manner as hydrophilic macromolecules can participate in the formation of a nanomatrix. The three-dimensional networks comprising hydrogels arise because of the fact that regularly ordered zones of chain molecules 11 assemble as so-called adhesive zones 40. A hydrogel formed in such a manner has the advantage that it is pervious to small molecules such as for example metabolites or water. The binding of water molecules and consequently the volume of the hydrogel depends on the fixed charges present in the hydrogel.

Figure 6A:
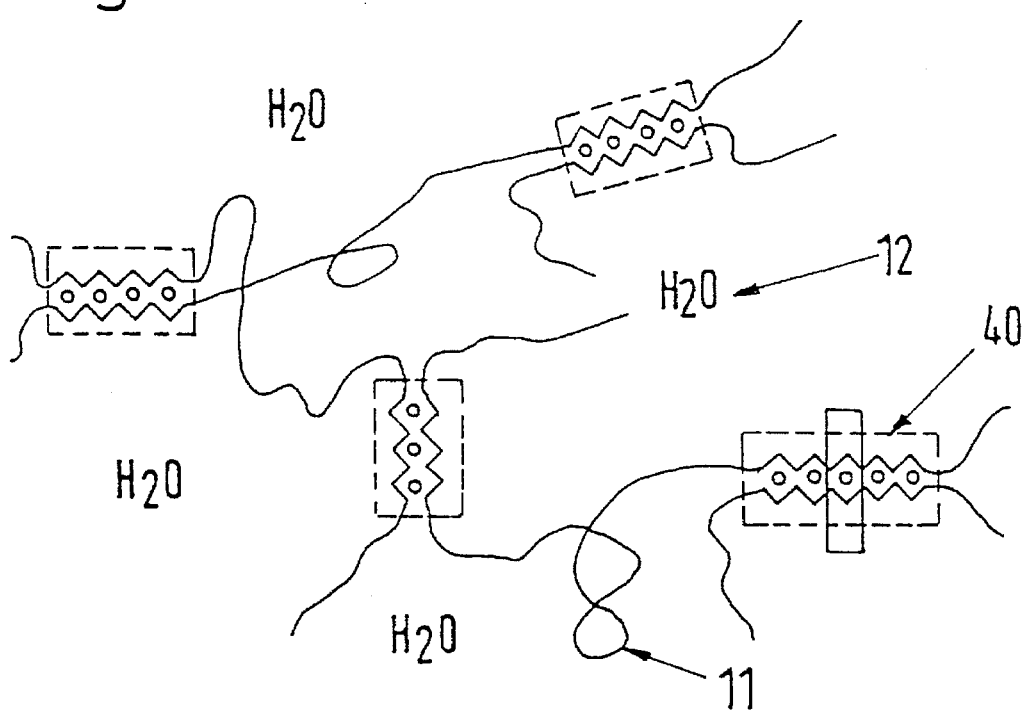
FIG. 6a schematically illustrates the three-dimensional network of a nanomatrix, for example alginate, in which the warp association occurs through complex formation with calcium ions.
Figure 6B:
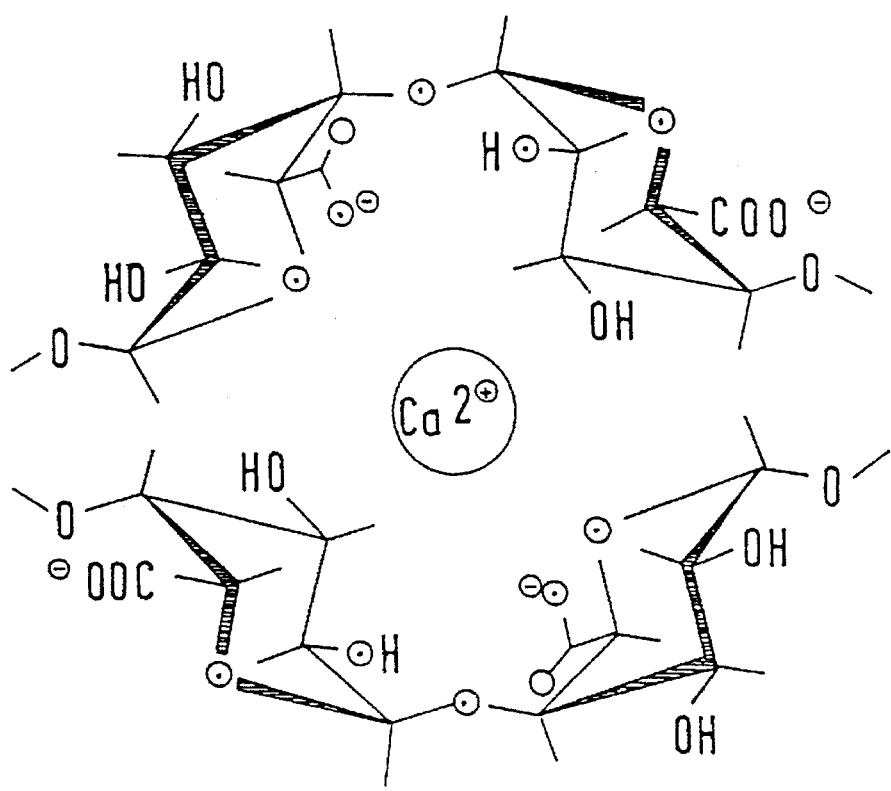
FIG. 6b illustrates the chelate-bonds of FIG. 6a in a representation which is conventional in chemistry.

One example of gel-forming compounds having fixed charges is the alginates which are built-up as polysaccharides from manuronic acid and galuronic acid in changing block sequences. In certain polysaccharides (for example alginate), the adhesive zones 40 occur such that the manuronic acid units which are present in zigzag-chains because of the axial-axial glycosidic bonds lie opposite to one another. This arrangement is then fixed through calcium ions which enter into bindings with the carboxyl and hydroxyl groups. This is schematically illustrated in FIG. 6b in which illustrates a complexed calcium ion. Such a cross-linkage is also schematically illustrated in FIG. 6a which shows the freely movable water molecules which are present as possible dipoles in the presence of fixed charges. Through controlled cross-linkage and through absorption or addition of water molecules, the volume of a nanomatrix within the micromatrix can be increased to elevate the internal pressure of the areal implant.

Figure 10:
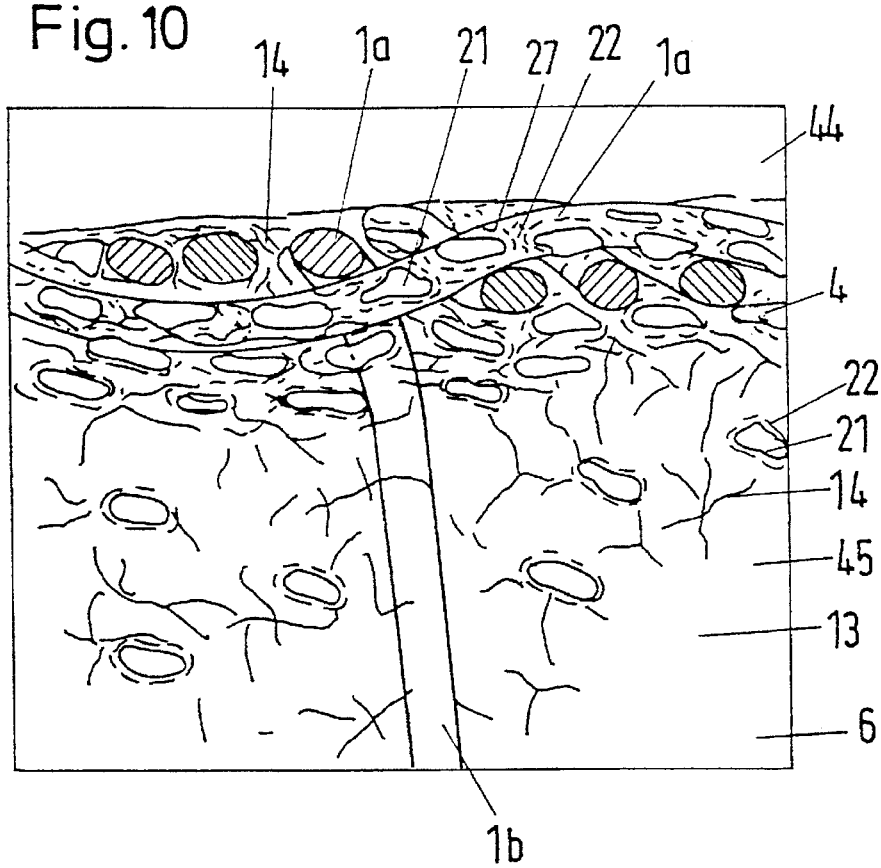
FIG. 10 schematically illustrates a section from an upper boundary layer with a nanomatrix which has cross-linked cells with an extracellular matrix.
Figure 7:
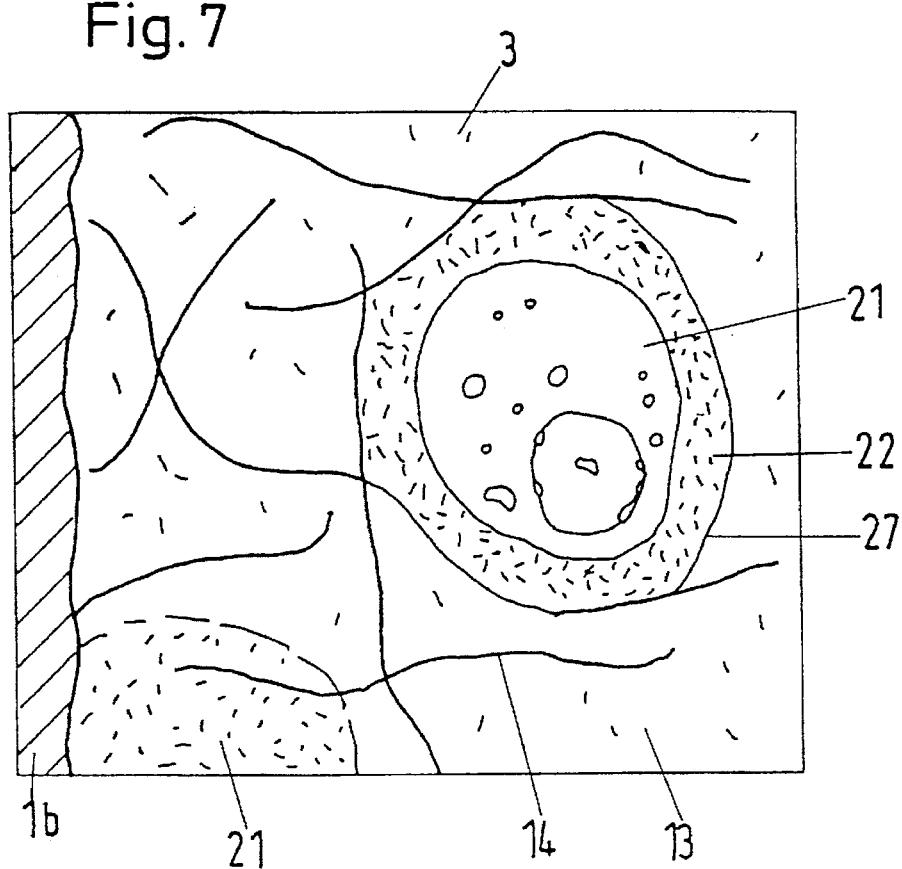
FIG. 7 illustrates a section from an intermediate layer with microfiber and nanomatrix which have cells with an extracellular matrix and collagen fibrils.

A micromatrix 2 of FIG. 1 which is embedded into a nanomatrix 3 has the advantage that the fibers 1b resist liquid displacement in the intermediate layer, so that an abrupt pressure load from the outside is principally transferred along the fibers 1b in the intermediate layer. Nevertheless, the edge of the implant must bear a similarly dense fiber connection as exists in a boundary layer 4, 5. This may be accomplished through the sewing of edges, through bonding of the edges or through attachment of support rings. These methods produce ravioli-like cushions which can be filled with a gel 13, comprising for example, an alginate. The implants can also be filled with a gel 13 and cells 22 which form an extracellular matrix. FIG. 7 shows a section of the intermediate layer 6 of such a cushion (implant). A cut fiber 1b lies within the gel 13, in which collagen fibers 14 and cells 21 lie in an extracellular matrix 22 which also comprises collagen fibrils 27. The growing of the extracellular matrix 22 alone brings about a respectable increase in volume within a implant in a few weeks in vitro. The cells 21 are chondrocytes which are distributed as evenly as possible in the nanomatrix 3 which is initially only filled with alginate. With increasing growth of the nanomatrix, proteoglycan-aggregates 46 and collagen fibers 14 are embedded which provide additional support and tensile strength. This is most strongly manifested in the region of the boundary layer b, 5, see FIG. 10, because there the chondrocytes and collagen fibers grow at high density because of the short distance to nutrients 44 which lie outside the implant in the synovial fluid.

Figure 8:
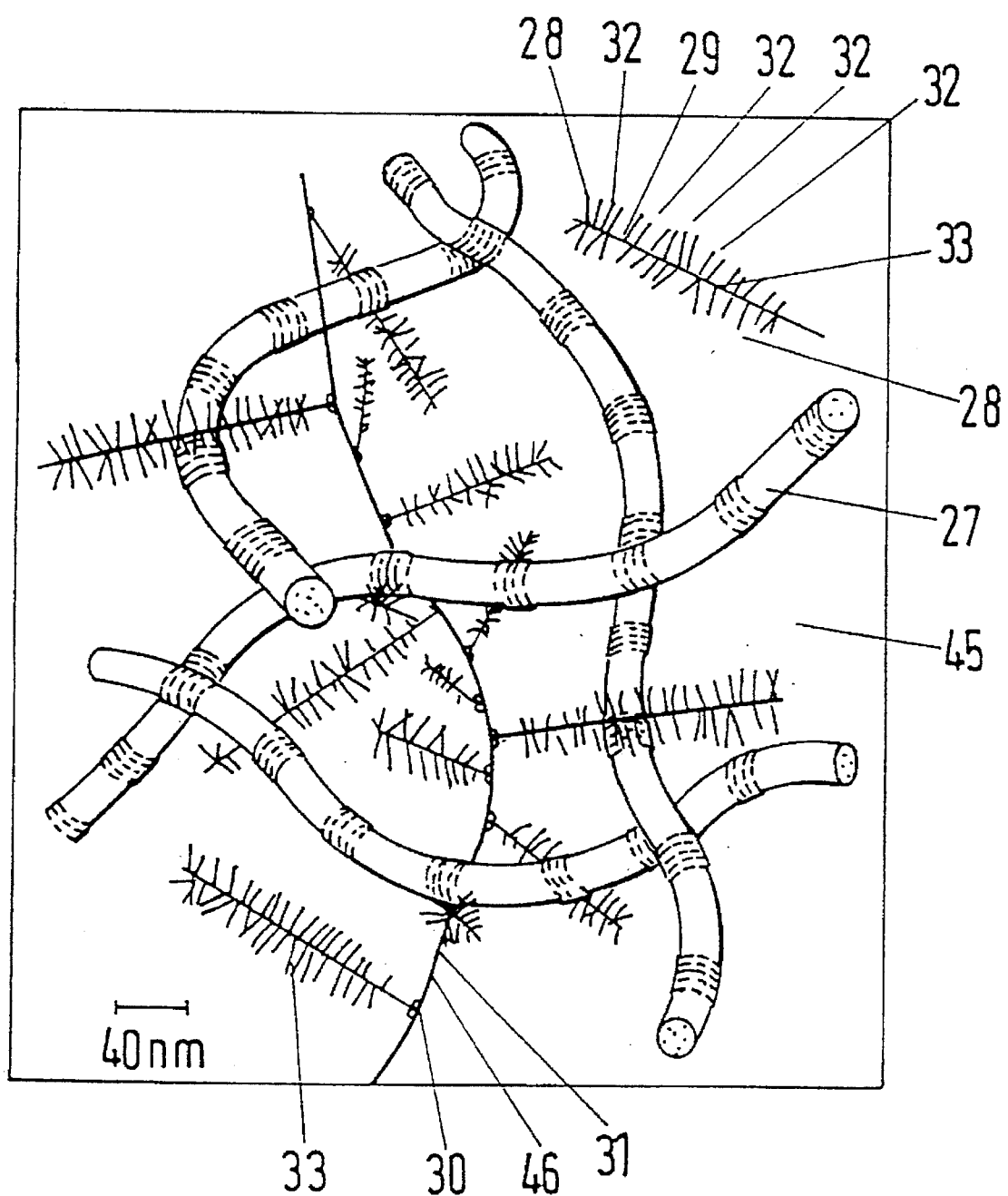
FIG. 8 illustrates schematically, an enlarged section of FIG. 7, in which the interacting collagen and proteoglycan networks are shown.

FIG. 8 shows an enlargement of the extracellular matrix 22 in which are dispersed proteoglycan-aggregates 46 and collagen fibrils 27. Water molecules 12 can initially freely move through the matrix. A small part of the water is bound to the collagen fibers 27 which are for example found in triple helix formations. Proteoglycan-monomers 33 are an additional component of the extracellular matrix. The proteoglycan monomers 33 comprise a protein core 29 to which are coupled linear polysaccharides 28. The linear polysaccharides carry the negative groups 32 ($SO_3^-COO^-$). The proteoglycan-monomers 33 are bound to hyaluronic acid threads 31 via link proteins 30 which unite the proteoglycan-aggregate 46 into a network. It is especially the proteoglycan monomers that bind water.

Positive ions, for example $Na^+$ are absorbed into the extracellular matrix to neutralize the bound negative charges. Thus, there are more osmotically active particles within the fabric (areal implant) than in the surrounding body fluid. The surplus of osmotically active particles within the areal implant leads to an osmotic pressure between the interstitial fluid 45 of the implant and the surrounding body fluid. This osmotic pressure increases the internal pressure of the areal implant which has a fixed (limited) volume.

The molecular weight of the proteoglycan-aggregates are of the magnitude of 50 to 100 million Daltons (Da). The proteoglycan-monomers 33 comprising a protein core 29 and attached polysaccharides 28 have a molecular weight ranging around 1 million Daltons, while the chain hyaluronic acids have molecular weights ranging around 2 to 6 million Daltons. The molecular weights of the aggregates can range up to 100 million Daltons when long chains 31 of hyaluronic acid onto which proteoglycan-aggregates are bound form.

We claim:

1. An implant for replacement of cartilagineous tissue, said implant comprising:
    a micromatrix (2) which is constructed from an upper boundary layer (4) and a lower boundary layer (5) wherein said upper and said lower boundary layers are connected via an intermediate layer (6) with fibers (1) having a diameter on the order of magnitude of micrometers; and
    a nanomatrix (3) situated within said intermediate layer (6), said nanomatrix matrix containing elements of a size on the order of magnitude of nanometers, and said nanomatrix containing cells dispersed therein, where said cells increase the volume of said nanomatrix (3) through synthesis of extracellular matrix; and
    wherein said intermediate layer (6) accommodates said nanomatrix (3) such that, for a growing inner pressure between said boundary layers (4, 5) said boundary layers are mutually held at a preset distance (7) from one another.

2. The implant of claim 1, wherein said cells are chondrocytes.

3. The implant of claim 1, wherein the boundary layers (4, 5) have a higher average fiber (1a or 1c) density than the average fiber (1b) density of said intermediate layer.

4. The implant of claim 3, wherein said fibers (1b) within said intermediate layer (6), by resisting said increase in volume of said micromatrix (2) cause an increase in internal pressure of said micromatrix (2).

5. The implant of claim 1, wherein said nanomatrix comprises chain molecules (11) dispersed therein, where said chain molecules (11) enlarge the volume of said nanomatrix (3) through the absorption of water molecules.

6. The implant of claim 5, wherein said chain molecules are proteoglycan aggregates (46) having molecular weights ranging from 50 to 100 million daltons.

7. The implant of claim 5, wherein said chain molecules are polysaccharides.

8. The implant of claim 1, wherein said nanomatrix (3) further comprises a gel (13) that keeps said dispersed cells phenotypically stable.

9. The implant of claim 1, wherein the fibers (1b) of the intermediate layer enter at least one boundary layer (4 or 5) where said fibers bend so as to lie in the plane of said boundary layer such that said boundary layer that has a higher average fiber (1a or 1c) density than the average fiber (1b) density of said intermediate layer.

10. The implant of claim 9, wherein the fiber (1b) enters into at least one boundary layer (4 or 5) where said fiber forms an arch (9).

11. The implant of claim 1 wherein at least one of said boundary layers (4 or 5) further comprises a membrane which is pervious to liquids.

12. The implant of claim 11, wherein said membrane is formed from polyurethane.

13. The implant of claim 1, wherein at least one of said boundary layers (4 or 5), is a biocompatible woven or knitted fabric.

14. The implant of claim 13, wherein said biocompatible woven or knitted fabric comprises a material selected from the group consisting of poyethyleneterephthalate, polyetherketone, polypropylene, teflon, carbon, and polyethylene.

15. The implant of claim 1, wherein said implant is manufactured through weaving or knitting in two planes (10a, 10b).

16. The implant of claim 15, wherein warp yarns (20a) of one plane (10a) differ from warp yarns (20b) in the other plane (10b) by titre or by the number of filaments in cross-section.

17. The implant of claim 15, wherein warp yarns (20a) of one plane (10a) differ from warp yarns (20b) in the other plane (10b) by material.

18. The implant of claim 15, wherein the warp yarns (20a) of one plane, (10a) are made from metal.

19. The implant of claim 18, wherein said metal is titanium.

20. The implant of claim 1, wherein said intermediate layer (6) comprises a material selected from the group consisting of a woven fabric, a knitted fabric, or a non-woven fabric.

21. The implant of claim 1, wherein a connection between said intermediate layer (6) and a boundary layer (4 or 5) is welded.

22. The implant of claim 1, wherein a connection between said intermediate layer (6) and a boundary layer (4 or 5) is produced through partial dissolution with a solvent.

23. The implant of claim 1, wherein a connection between said intermediate layer (6) and a boundary layer (4 or 5) is an adhesive bond.

24. The implant of claim 1, wherein a connection between said intermediate layer (6) and a boundary layer (4 or 5) is a sewn connection.

25. The implant of claim 1, wherein said nanomatrix comprises collagen fibers.

26. The implant of claim 1, wherein said intermediate layer (6) comprises a biologically decomposable material.

27. The implant of claim 26, wherein said biologically decomposable material is selected from the group consisting of a polylactic acid, a polyglycolic acid, ε-caprolactone, polydioxanone, a polylactic acid copolymer, a polyglycolic acid copolymer, an ε-caprolactone copolymer, a polydioxanone copolymer, a polylactic acid mixed polymer, a polyglycolic acid mixed polymer, an ε-caprolactone mixed polymer, and a polydioxanone mixed polymer.

28. An implant for replacement of cartilagineous tissue, said implant comprising:
   a micromatrix (2) which is constructed from an upper boundary layer (4) and a lower boundary layer (5) wherein said upper and said lower boundary layers are connected via an intermediate layer (6) with fibers (1) having a diameter on the order of magnitude of micrometers; and
   a nanomatrix (3) situated within said intermediate layer (6), said nanomatrix matrix containing elements of a size on the order of magnitude of nanometers, and wherein said nanomatrix (3) comprises collagen fibers; and
wherein said intermediate layer (6) accommodates said nanomatrix (3) such that, for a growing inner pressure between said boundary layers (4, 5) said boundary layers are mutually held at a preset distance (7) from one another.

29. The implant of claim 28, wherein said collagen fibers comprise up to 15% dry weight of said nanomatrix (3).

30. The implant of claim 28, wherein said nanomatrix comprises chain molecules (11) dispersed therein, where said chain molecules (11) enlarge the volume of said nanomatrix (3) through the absorption of water molecules.

31. The implant of claim 30, wherein said chain molecules are proteoglycan aggregates (46) having molecular weights ranging from 50 to 100 million daltons.

32. The implant of claim 30, wherein said chain molecules are polysaccharides.

33. The implant of claim 30, wherein said nanomatrix further comprises cells dispersed therein.

34. The implant of claim 33, wherein said cells are chondrocytes.

35. The implant of claims 33, wherein said nanomatrix (3) further comprises a gel (13) that keeps said cells phenotypically stable.

36. The implant of claim 28, wherein the fibers (1b) of the intermediate layer enter at least one boundary layer (4 or 5) where said fibers bend so as to lie in the plane of said boundary layer such that said boundary layer has a higher average fiber (1a or 1c) density than the average fiber (1b) density of said intermediate layer.

37. The implant of claim 28, wherein the fiber (1b) enters into at least one boundary layer (4 or 5) where said fiber forms an arch (9).

38. The implant of claim 28, wherein at least one of said boundary layers (4 or 5) further comprises a membrane which is pervious to liquids.

39. The implant of claim 38 wherein said membrane is formed from polyurethane.

40. The implant of claim 28, wherein at least one of said boundary layers (4 or 5) is a biocompatible woven or knitted fabric.

41. The implant of claim 40, wherein said biocompatible woven or knitted fabric comprises a material selected from the group consisting of poyethyleneterephthalate, polyetherketone, polypropylene, teflon, carbon, and polyethylene.

42. The implant of claim 28, wherein said intermediate layer (6) comprises a material selected from the group consisting of a woven fabric, a knitted fabric, or a non-woven fabric.

43. The implant of claim 28, wherein said intermediate layer (6) comprises a biologically decomposable material.

44. The implant of claim 43, wherein said biologically decomposable material is selected from the group consisting of polylactic acid, a polyglycolic acid, ε-caprolactone, polydioxanone, a polylactic acid copolymer, a polyglycolic acid copolymer, an ε-caprolactone copolymer, a polydioxanone copolymer, a polylactic acid mixed polymer, a polyglycolic acid mixed polymer, an ε-caprolactone mixed polymer, and a polydioxanone mixed polymer.

45. An implant for replacement of cartilagineous tissue, said implant comprising:

a micromatrix (2) which is constructed from an upper boundary layer (4) and a lower boundary layer (5) wherein said upper and said lower boundary layers are connected via an intermediate layer (6) with fibers (1) having a diameter on the order of magnitude of micrometers; and a nanomatrix (3) situated within said intermediate layer (6), said nanomatrix matrix containing elements of a size on the order of magnitude of nanometers;

wherein said nanomatrix comprises absorbed water molecules dispersed therein and wherein said intermediate layer (6) accommodates said nanomatrix (3) such that, for a growing inner pressure between said boundary layers (4, 5) said boundary layers are mutually held at a preset distance (7) from one another.

46. The implant of claim 45, wherein said nanomatrix further comprises chain molecules (11) dispersed therein, where said chain molecules (11) enlarge the volume of said nanomatrix (3) through the absorption of water molecules.

47. The implant of claim 46, wherein said chain molecules are proteoglycan aggregates (46) having molecular weights ranging from 50 to 100 million daltons.

48. The implant of claim 46, wherein said chain molecules are polysaccharides.

49. The implant of claim 45, wherein the fibers (1b) of the intermediate layer enter at least one boundary layer (4 or 5) where said fibers bend so as to lie in the plane, of said boundary layer such that said boundary layer has a higher average fiber (1a or 1c) density than the average fiber (1b) density of said intermediate layer.

50. The implant of claim 45, wherein the fiber (1b) enters into at least one boundary layer (4 or 5) where said fiber forms an arch (9).

51. The implant of claim 45, wherein at least one of said boundary layers (4 or 5) further comprises a membrane which is pervious to liquids.

52. The implant of claim 51 wherein said membrane is formed from polyurethane.

53. The implant of claim 45 wherein at least one of said boundary layers (4 or 5) is a biocompatible woven or knitted fabric.

54. The implant of claim 53, wherein said woven or knitted fabric comprises a material selected from the group consisting of poyethylene-terephthalate, polyetherketone, polypropylene, teflon, carbon, and polyethylene.

55. The implant of claim 45, wherein said intermediate layer (6) comprises a material selected from the group consisting of a woven fabric, a knitted fabric, or a non-woven fabric.

56. The implant of claim 45, wherein said intermediate layer (6) comprises a biologically decomposable material.

57. The implant of claim 56, wherein said biologically decomposable material is selected from the group consisting of a polylactic acid, a polyglycolic acid, ε-caprolactone, polydioxanone, a polylactic acid copolymer, a polyglycolic acid copolymer, an ε-caprolactone copolymer, a polydioxanone copolymer, a polylactic acid mixed polymer, a polyglycolic acid mixed polymer, an ε-caprolactone mixed polymer, and a polydioxanone mixed polymer.

* * * * *